(12) United States Patent
Nelson et al.

(10) Patent No.: US 12,390,299 B2
(45) Date of Patent: Aug. 19, 2025

(54) SEALER DIVIDER

(71) Applicant: GYRUS ACMI, INC., Southborough, MA (US)

(72) Inventors: Jeffrey Nelson, Plymouth, MN (US); Kester Julian Batchelor, Mound, MN (US); Nikhil M. Murdeshwar, Maple Grove, MN (US); Eric J. Boone, Saint Michael, MN (US); Christian J. Fiksen, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 836 days.

(21) Appl. No.: 17/267,741

(22) PCT Filed: Aug. 12, 2019

(86) PCT No.: PCT/US2019/046161
§ 371 (c)(1),
(2) Date: Feb. 10, 2021

(87) PCT Pub. No.: WO2020/033950
PCT Pub. Date: Feb. 13, 2020

(65) Prior Publication Data
US 2021/0307859 A1    Oct. 7, 2021

Related U.S. Application Data

(60) Provisional application No. 62/717,169, filed on Aug. 10, 2018.

(51) Int. Cl.
*A61B 18/00*    (2006.01)
*A61B 18/12*    (2006.01)
(Continued)

(52) U.S. Cl.
CPC .......... *A61B 90/03* (2016.02); *A61B 18/1445* (2013.01); *A61B 2018/00083* (2013.01);
(Continued)

(58) Field of Classification Search
None
See application file for complete search history.

(56) References Cited

U.S. PATENT DOCUMENTS 8,496,656 B2    7/2013    Shields et al.
2009/0149853 A1*    6/2009    Shields .............. A61B 18/1445
606/51

(Continued)

FOREIGN PATENT DOCUMENTS

CN    112996450 A    6/2021
JP    2000102545    4/2000
(Continued)

OTHER PUBLICATIONS

"European Application Serial No. 119759221.5, Response Filed Nov. 10, 2021 to Communication Pursuant to Rules 161 (1) and 162 mailed Apr. 30, 2021", 10 pgs.

(Continued)

*Primary Examiner* — Linda C Dvorak
*Assistant Examiner* — Nicholas S Borsch
(74) *Attorney, Agent, or Firm* — Schwegman Lundberg & Woessner, P.A.

(57)    ABSTRACT

A device comprising: a first jaw having a gripping surface; a second jaw having a gripping surface, the second jaw being spaced apart from the first jaw and being configured to move between an open position and a closed position, and a sealer divider having a plurality of stops including at least: one or more distal stops, one or more proximal stops; and one or more intermediate stops that are of an intermediate height when compared to a height of the one or more distal (Continued)

stops and a height the one or more proximal stops, and wherein the plurality of stops are non-conductive and are distributed on the gripping surface of the first jaw, the gripping surface of the second jaw, or both, and wherein the first jaw and the second jaw have a proximal end and a distal end and the plurality of stops produce a gap that is widest at the proximal end and tapers so that a gap at the distal end is narrower than the gap at the proximal end.

21 Claims, 9 Drawing Sheets

(51) Int. Cl.
*A61B 18/14* (2006.01)
*A61B 90/00* (2016.01)

(52) U.S. Cl.
CPC . *A61B 2018/0063* (2013.01); *A61B 2018/126* (2013.01); *A61B 2018/1455* (2013.01); *A61B 2090/035* (2016.02)

(56) References Cited

U.S. PATENT DOCUMENTS

| | | | | |
|---|---|---|---|---|
| 2009/0248021 | A1* | 10/2009 | McKenna | A61B 18/1445 606/51 |
| 2016/0175028 | A1* | 6/2016 | Trees | A61B 18/1445 606/52 |
| 2017/0312014 | A1* | 11/2017 | Strobl | A61B 18/1442 |
| 2017/0312016 | A1 | 11/2017 | Strobl et al. | |
| 2017/0312018 | A1* | 11/2017 | Trees | A61B 18/1445 |
| 2018/0126149 | A1 | 5/2018 | Vaders et al. | |
| 2019/0175256 | A1* | 6/2019 | Butler | A61B 17/2909 |

FOREIGN PATENT DOCUMENTS

| | | |
|---|---|---|
| JP | 2004532676 | 10/2004 |
| JP | 2013150828 | 8/2013 |
| JP | 2011005271 | 11/2017 |
| JP | 7459100 | 3/2024 |
| WO | 2017181092 | 10/2017 |
| WO | WO-2020033950 A1 | 2/2020 |

OTHER PUBLICATIONS

"Japanese Application Serial No. 2021-531625, Notification of Reasons for Refusal mailed May 8, 2023", w English Translation, 13 pgs.

"Japanese Application Serial No. 2021-531625, Response filed Aug. 4, 2023 to Notification of Reasons for Refusal mailed May 8, 2023", w english claims, 15 pgs.

"Chinese Application Serial No. 201980059174.6, Notification to Make Rectification mailed Apr. 9, 2021", with machine translation, 2 pgs.

"Chinese Application Serial No. 201980059174.6, Response filed May 18, 2021 to Notification to Make Rectification mailed Apr. 9, 2021", with machine translation, 7 pgs.

"Japanese Application Serial No. 2021-531625, Notification of Reasons for Refusal mailed Aug. 28, 2023", w English translation, 13 pgs.

"Chinese Application Serial No. 201980059174.6, Office Action mailed Sep. 20, 2023", W English Translation, 23 pgs.

"International Application Serial No. PCT/US2019/046161, International Search Report mailed Nov. 28, 2019", 4 pgs.

"International Application Serial No. PCT/US2019/046161, Written Opinion mailed Nov. 28, 2019", 8 pgs.

"European Application Serial No. 19759221.5, Communication Pursuant to Article 94(3) EPC mailed Dec. 19, 2023", 3 pgs.

"Japanese Application Serial No. 2021-531625, Response filed Nov. 24, 2023 to Notification of Reasons for Refusal mailed Aug. 28, 2023", w/ english claims, 20 pgs.

"Chinese Application Serial No. 201980059174.6, Response filed Feb. 4, 2024 to Office Action mailed Sep. 20, 2023", w english claims, 12 pgs.

"Chinese Application Serial No. 201980059174.6, Decision of Rejection mailed Mar. 19, 2024", w English translation, 18 pgs.

"European Application Serial No. 19759221.5, Response filed Apr. 16, 2024 to Communication Pursuant to Article 94(3) EPC mailed Dec. 19, 2023", 8 pgs.

"Chinese Application Serial No. 201980059174.6, Request for Reexamination filed Apr. 30, 2024", with English claims, 24 pgs.

\* cited by examiner

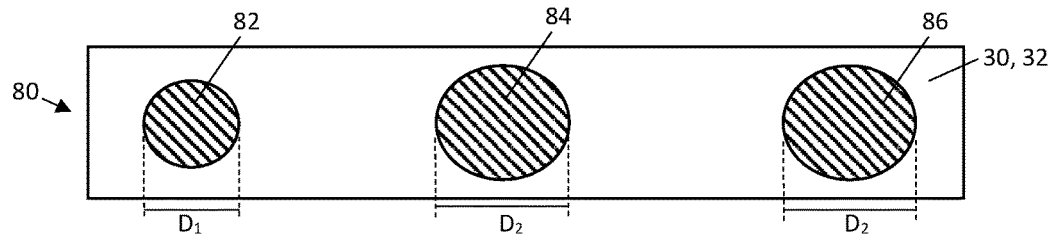
Figure 12B
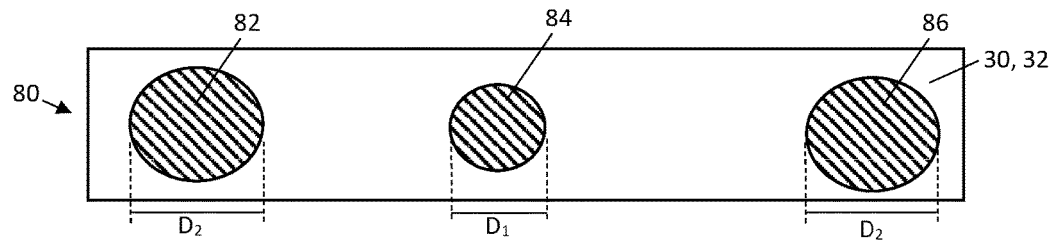
Figure 12C
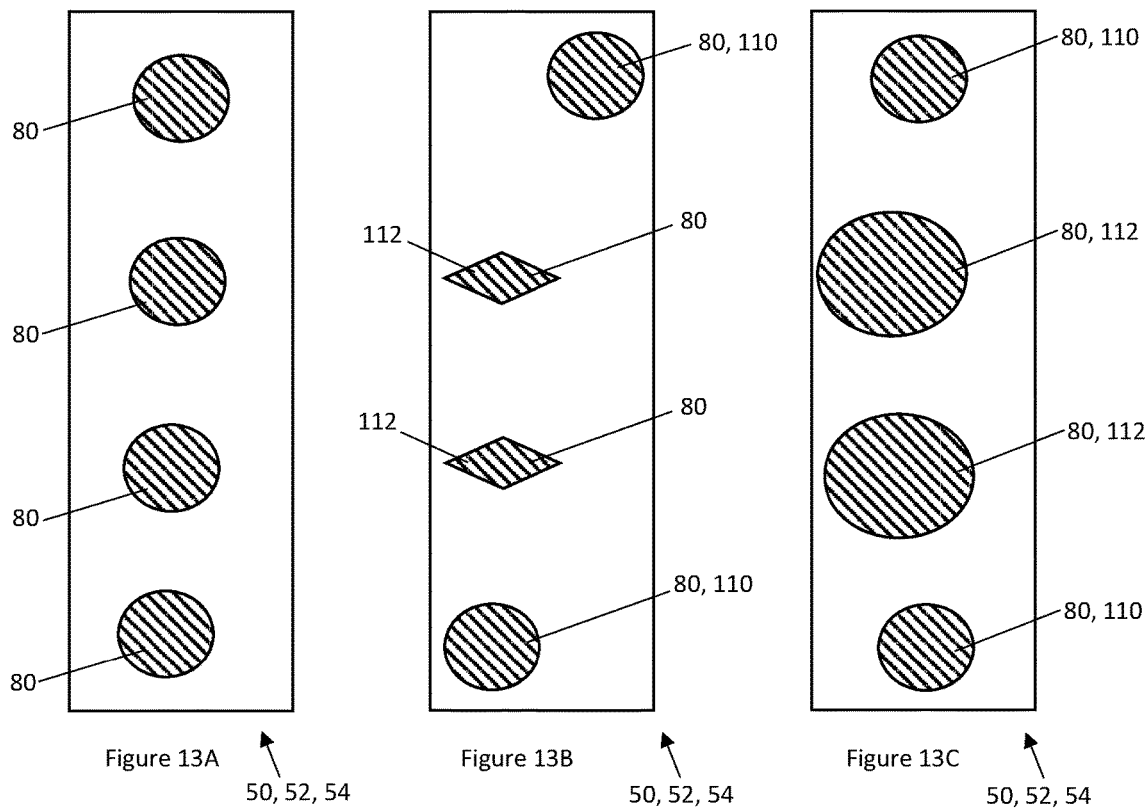
Figure 13A
Figure 13B
Figure 13C

SEALER DIVIDER

CROSS-REFERENCE TO RELATED APPLICATIONS

This application is a U.S. National Stage Filing under 35 U.S.C. 371 from International Application No. PCT/US2019/046161, filed on 12 Aug. 2019, and published as WO 2020/033950 A1 on 13 Feb. 2020, which claims the benefit of U.S. Provisional Patent Application No. 62/717,169 filed on 10 Aug. 2018, all of which are incorporated herein by reference in their entireties.

FIELD

The present teachings provide electrosurgical forceps including a sealer divider having one or more spacing stops and preferably a plurality of spacing stops that assist in preventing components of the electrosurgical forceps from coming into contact, being shorted, or both.

BACKGROUND

Bipolar electrosurgical forceps may have a pair of jaws, each jaw having a sealing surface facing the opposite jaw. It may be desirable for the surfaces to be prevented from coming into direct contact with each other so that an electrical short is not created between the sealing surfaces, i.e. two electrodes. One structure that may be used is one or more stops placed on one or both of the jaws. The stops may be made from an electrically nonconductive material. This is to prevent sealing surfaces from contacting and creating 'short circuits' when the two electrically conductive surfaces meet and becoming a preferential path for energy during electrosurgical sealing. This also includes the desire to maintain a specific but varied gap between the device contacting conducting surfaces that allows for thin tissues to be grasped and electrically modified in one area of the jaw, while allowing thicker vessels to be adequately effected in other parts of the jaw. These thickness requirements do overlap, but these varying standoff heights do provide advantages to the user. These gaps can range between 0.001 inches to 0.010 inches, depending on the desired tissue effect. The gap between the sealing surfaces may be substantially uniform, or the gap may be tailored for a varied width along the length of the jaws. The gap may be wider at the proximal end of the jaw and narrower at the distal end, or the gap may be narrower at the proximal end of the jaws and wider at the distal end. The width of the gap may vary linearly along the length of the jaws or it may vary in a non-linear fashion.

Uniform gaps may not provide for the varying manner that different tissues may need to be manipulated. It may be beneficial to have a non-uniform gap. And specifically, it may be beneficial for the distal end of the jaws to be closer than the proximal end so that tissue is better retained. Some attempts to create electrosurgical devices may be found in U.S. Pat. Nos. 5,403,312; 5,443,463; 5,891,142; 9,603,655; 10,251,696; and 10,265, 121 the teachings of which are expressly incorporated by reference herein for all purposes.

It would be desirable to have a device that that creates a dielectric space between two sealing surfaces while assisting in gripping a feature of interest there between. What is needed is a sealer divider that grips a feature of interest without damaging the feature of interest and prevents shorting between two opposing sealing surfaces. It would be desirable to have a sealer divider with one or more stops that create a gap between two or more sealing surfaces. What is needed is forceps that grip a feature of interest and substantially equally distribute a force across the opposing faces of the forceps.

SUMMARY

The present teachings provide: a device comprising: a first jaw member having a first seal surface, a second jaw member having a second seal surface opposing the first seal surface, at least one first stop member spaced-apart along at least a portion of the length of the first seal surface, and at least one second stop members spaced-apart along at least a portion of the length of the second seal surface.

The present teachings provide: A device comprising: a first jaw having a gripping surface; a second jaw having a gripping surface, the second jaw being spaced apart from the first jaw and being configured to move between an open position and a closed position, and a sealer divider having a plurality of stops including at least: one or more distal stops, one or more proximal stops; and one or more intermediate stops that are of an intermediate height when compared to a height of the one or more distal stops and a height the one or more proximal stops, and wherein the plurality of stops are non-conductive and are distributed on the gripping surface of the first jaw, the gripping surface of the second jaw, or both, and wherein the first jaw and the second jaw have a proximal end and a distal end and the plurality of stops produce a gap that is widest at the proximal end and tapers so that a gap at the distal end is narrower than the gap at the proximal end.

The present teachings provide: a device comprising: a first jaw having a gripping surface; a second jaw having a gripping surface, the second jaw being spaced apart from the first jaw and being configured to move between an open position and a closed position, and a sealer divider having a plurality of stops including at least: one or more distal stops having a height, one or more proximal stops having a height; and one or more intermediate stops located on the first jaw and the second jaw with some of the one or more intermediate stops being located in an opposed position so that when the first jaw and the second jaw are closed the some of the one or more intermediate stops on the first jaw contact the some of the one or more intermediate stops on the second jaw to have a combined height that is greater than the height of the one or more distal stops, the height of the one or more proximal stops, or both, and wherein the plurality of stops are non-conductive and the one or more distal stops, the one or more proximal stops, or both are distributed on the gripping surface of the first jaw, the gripping surface of the second jaw, or both.

The present teachings provide a bipolar electrosurgical device comprising a housing, an elongated shaft extending from the housing, and opposing first and second jaw members disposed at a distal end of the elongated shaft; at least one of the first or second jaw members is movable relative to the other from a first position wherein the first and second jaw members are disposed in spaced relation relative to one another to a second position wherein the first and second jaw members are closer to one another; the first and second jaw members include first and second sealing surfaces, respectively, extending along a respective length thereof; the first and second sealing surfaces are adapted to connect to a source of electrical energy, which could be individually or in combination RF, Ultrasonic or Microwave, such that the first and second seal surfaces are capable of conducting energy through tissue held therebetween. The first seal surface includes a knife channel defined therein and extending along a length thereof. The second seal surfaces include a knife channel defined therein and extending along a length thereof; the knife channels of the first and second seal surfaces are configured to align with one another in the second position of the first and second jaw members to permit translation of the knife therethrough. A knife is configured to translate through the knife channel. There is a single first stop member on the first seal surface, or a plurality of first stop members spaced-apart along at least a portion of the length of the first seal surface. There is a single second stop members on the second seal surface, or a plurality of second stop members spaced-apart along at least a portion of the length of the second seal surface. The first stop member, or members, protrude a first distance from the first seal surface and the second stop member, or members, protrudes a second distance from the second seal surface. The second distance is greater than the first distance.

The present teachings provide: a bipolar electrosurgical instrument comprising a housing, an elongated shaft extending from the housing, and opposing first and second jaw members disposed at a distal end of the elongated shaft; at least one of the first or second jaw members is movable relative to the other from a first position wherein the first and second jaw members are disposed in spaced relation relative to one another to a second position wherein the first and second jaw members are closer to one another. The first and second jaw members include first and second sealing surfaces, respectively, extending along a respective length thereof. The first and second sealing surfaces are adapted to connect to a source of electrical energy such that the first and second seal surfaces are capable of conducting energy through tissue held therebetween. The first seal surface includes a knife channel defined therein and extending along a length thereof. A knife is configured to translate through the knife channel. There is a plurality of first stop members spaced-apart along at least a portion of the length of the first seal surface. There is a plurality of second stop members extending from the second seal surface. The second stop members have generally the same protrusion (height) as the first stop members. Select, or all, second stop members are positioned opposing the first stop members to combine, or stack up, creating opposing stop members of generally a greater combined protrusion than those placed upon the first or second seal surface.

The teachings herein provide a bipolar electrosurgical device comprising a housing, an elongated shaft extending from the housing, and opposing first and second jaw members disposed at a distal end of the elongated shaft. At least one of the first or second jaw members is movable relative to the other from a first position wherein the first and second jaw members are disposed in spaced relation relative to one another to a second position wherein the first and second jaw members are closer to one another. The first and second jaw members include first and second sealing surfaces, respectively, extending along a respective length thereof. The first and second sealing surfaces are adapted to connect to a source of electrical energy such that the first and second seal surfaces are capable of conducting energy through tissue held therebetween. The first seal surface includes a knife channel defined therein and extending along a length thereof. A knife is configured to translate through the knife channel. There is a single first stop member on the first seal surface, or a plurality of first stop members spaced-apart along at least a portion of the length of the first seal surface. There is a single second stop members on the second seal surface, or a plurality of second stop members spaced-apart along at least a portion of the length of the second seal surface. The first stop members provide a first compressibility from the first seal surface and the second stop members provide a second compressibility from the second seal surface.

The teachings herein provide a bipolar electrosurgical instrument comprising a housing, an elongated shaft extending from the housing, and opposing first and second jaw members disposed at a distal end of the elongated shaft. At least one of the first or second jaw members is movable relative to the other from a first position wherein the first and second jaw members are disposed in spaced relation relative to one another to a second position wherein the first and second jaw members are closer to one another. The first and second jaw members include first and second sealing surfaces, respectively, extending along a respective length thereof. The first and second sealing surfaces are adapted to connect to a source of electrical energy, such that the first and second seal surfaces are capable of conducting energy through tissue held therebetween. The first seal surface includes a knife channel defined therein and extending along a length thereof. A knife is configured to translate through the knife channel. There is a plurality of first stop members, spaced-apart along at least a portion of the length of the first seal surface. There is a plurality of second stop members extending from the second seal surface. The second stop members have generally the same compression as the first stop members. Select second stop members are positioned opposing the first stop members to combine creating opposing stop members of generally a greater combined compression and protrusion than those placed upon the first or second seal surface.

The teachings herein provide a device that that creates a dielectric space between two sealing surfaces while assisting in gripping a feature of interest there between. The teachings herein provide a sealer divider that grips a feature of interest without damaging the feature of interest and prevents shorting between two opposing sealing surfaces. The teachings herein provide a sealer divider with one or more stops that create a gap between two or more sealing surfaces. The teachings herein provide forceps that grip a feature of interest and substantially equally distribute a force across the opposing faces of the forceps.

BRIEF DESCRIPTION OF THE DRAWINGS

FIG. 12B illustrates a variation in sizes of the stops in each region.

FIG. 12C illustrates a variation in sizes of the stops in each region.

FIG. 13A illustrates the position of stops within a region relative to each other.

FIG. 13B illustrates the position of stops within a region relative to each other and shapes of the stops.

FIG. 13C illustrates the position of stops within a region relative to each other and size differences of the stops.

DETAILED DESCRIPTION

Figure 1:
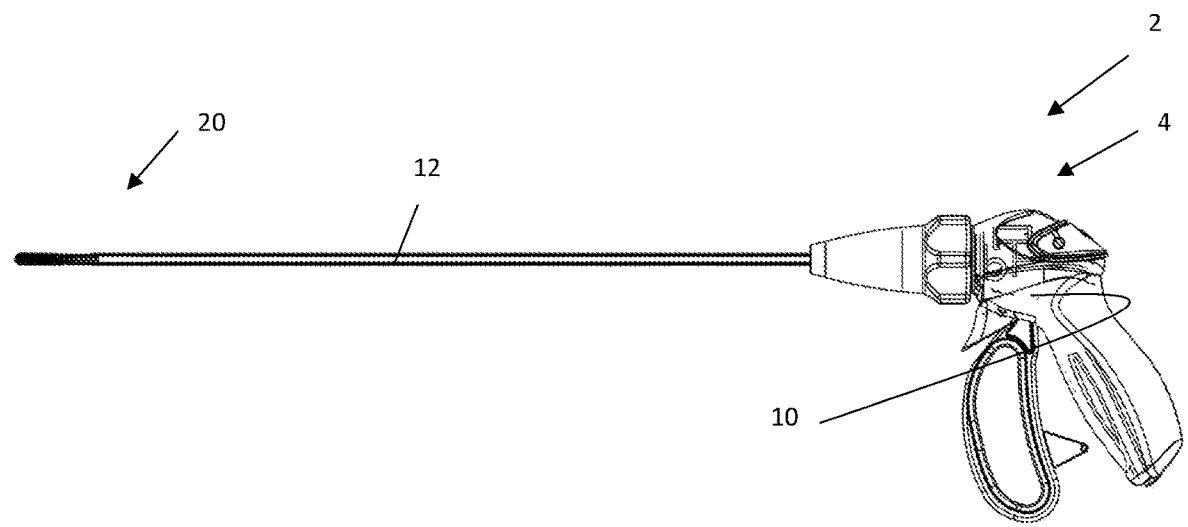
FIG. 1 is a side view of the device with the jaws in the closed position.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide an electrosurgical device. The electrosurgical device functions to grip tissue or an anatomical feature of interest. The electrosurgical device functions to cut, cauterize, or both tissue, a vein, an artery, an anatomical feature of interest, or a combination hereof. The electrosurgical device may be used for open surgery. Preferably, the electrosurgical device is used in laparoscopic surgery. The electrosurgical device may be electrosurgical forceps.

The electrosurgical forceps may function to grip tissue or an anatomical feature of interest (e.g., vein or artery); cut tissue or an anatomical feature; cauterize tissue or an anatomical feature; or a combination thereof. The electrosurgical forceps may be bias open, or bias closed. The electrosurgical forceps may conduct or produce bipolar energy, monopolar energy, or both. The electrosurgical forceps may grip tissue or an anatomical feature without damaging the tissue or the anatomical feature. The electrosurgical forceps may have a distal end and a proximal end. The electrosurgical forceps may include two opposing jaws, a knife, a housing, or a combination thereof.

The housing may function to be an end that a user holds to control the forceps, perform a surgical procedure, or both. The housing may house mechanical components, electrical components, or both. The housing may be at a proximal end. The housing may be made of metal, plastic, a polymer, or a combination thereof. The housing may control one or more devices a distal end of the electrosurgical device. The housing may have one or more levers that when actuated move one or more members at a distal end of the surgical device. For example, the housing may include a jaw lever that moves a first jaw, a second jaw, or both. In another example, the housing may include a knife lever that moves a knife. The housing may be partially or entirely held within a hand. The housing may house one or more mechanical components that move one or more jaws, one or more knives, or both. The housing may be static and one or more movable components may move about a portion of the housing or an elongated shaft (e.g., a stylet) that extends from the housing.

The elongated shaft may function to extend a distal end, working components, or both through an incision, aperture, orifice, a small opening, trocar, or a combination thereof to a location of interest. The elongated shaft may permit the electrosurgical device to be used for laparoscopic surgery. The elongated shaft may connect the housing to the forceps, first jaw, second jaw, the knife, or a combination thereof. The elongated shaft may support, control, or both the forceps, the jaws, the knife, or a combination thereof. The elongated shaft may be made of metal, plastic, a biocompatible material, a natural material, a synthetic material, or a combination thereof. The elongated shaft may be sufficiently rigid so that the forceps, the knife, or both may be moved and manipulated without being damaged during use, while inside of a patient, or both. The elongated shaft may support the forceps so that the forceps may be actuated and used to perform a surgical procedure.

The forceps may function to grip, hold, remove, cut, cauterize, coagulate, implant, or a combination thereof tissue, a feature of interest, an anatomical feature of interest, or a combination thereof. The forceps may open and close. The forceps may grip or hold items when the forceps are closed. The forceps may apply a therapy current when the forceps are closed (e.g., bipolar energy). The forceps may cut, cauterize, coagulate, or a combination thereof when the forceps apply a therapy current. The forceps may have one or more movable members (e.g., jaws). The forceps may have a pivot member. The forceps may operate by one or both jaws rotating about a pivot member.

The one or more pivot members function to permit relative movement of one or more jaws relative to another of the one or more jaws. The pivot member may connect two jaws together. The pivot members may connect each jaw individually to the elongated shaft. The pivot member may be a pin that a proximal end of each jaw pivots about. The one or more pivot members may restrict or prevent axial movement of the jaws. One jaw may include a pivot member and one jaw may be free of a pivot member. Only one jaw may include or be connected to a pivot member. The one or more pivot members may permit the forceps to move between an open position and a closed position. The pivot may assist in creating a gripping force. The electrosurgical device may include one or more pivot members. The electrosurgical device may include a plurality of pivot members. The electrosurgical device may include a pivot member for each jaw. The pivot member may allow movement in one manner, or one plane. For example, the pivot member may allow for rotational movement but prevent axial movement (e.g., longitudinal), vertical movement, side to side movement, or a combination thereof. The pivot member (e.g., pivot) may allow one or more knives to extend distal of the forceps, be retracted into the jaws, or both. The one or more pivot members may permit movement of a first jaw, a second jaw, or both of the forceps.

Preferably, the forceps comprise a first and second jaw. The first jaw, the second jaw, or both (e.g., jaws) may function to grip, cut, cauterize, coagulate, hold, insert, remove, or a combination thereof tissue, an anatomical feature, a feature of inters, or a combination thereof. The jaws may be rigid so that the jaws may grip and hold a feature of interest. For example, the jaws may grip a vein or tissue during a procedure. The jaws may hold a feature of interest so that a knife may cut the feature of interest. The jaws may grip and a cauterize a feature of interest. The first jaw, the second jaw, or both may be used as a probe to move tissue, a feature of interest, an anatomical feature, or a combination thereof. The first jaw, the second jaw, or both may include one or more knife channels. The knife channels may be sufficiently large so that a knife may extend between the first jaw and the second jaw when the first jaw and the second jaw are closed. The first jaw may rotate relative to the second jaw. The second aw may be fixed. The first jaw may be movable both rotationally and axially. The one or more jaws may have a range of motion that is restricted by one or more stops. The jaws may include a distal end region, an intermediate region, a proximal region, or a combination thereof. The distal end region may extend from a distal tip towards the proximal end a distance of about 20 percent a length or more, about 25 percent a length or more, about 30 percent a length or more, about 50 percent a length or less, or about 45 percent a length or less of the jaw. The proximal end region may extend from a proximal tip towards the distal end a distance of about 20 percent a length or more, about 25 percent a length or more, about 30 percent a length or more, about 50 percent a length or less, or about 45 percent a length or less of the jaw. An intermediate region may be located between the distal end region and the proximal end region. The intermediate region may be the largest region. The intermediate region may be divided into two or more regions (e.g., a distal intermediate region and a proximal intermediate region). The intermediate region may be a same size as the proximal end region and the distal end region. The intermediate region may be located between a proximal end region and the distal end region and have a distance of about 20 percent a length or more, about 25 percent a length or more, about 30 percent a length or more, about 75 percent a length or less, about 60 percent a length or less, or about 50 percent or less of the jaw. The first jaw and second jaw when in a closed position may apply a therapy current and via one or more sealing surfaces.

The one or more sealing surfaces may function to apply a therapy current. The one or more sealing surfaces may apply monopolar energy. The one or more sealing surfaces may apply bipolar energy. The one or more sealing surfaces may be located on a first jaw, the second jaw, or both. Preferably the first jaw includes a first sealing surface and the second jaw includes a second sealing surface. The first sealing surface and the second sealing surface may be made of different materials. Preferably, the first sealing surface and the second sealing surface may be made of the same material. The first sealing surface and the second sealing surface may be conductive. The first sealing surface and the second sealing surface may have a material with different resistances or conductivity. During operation power may flow from the first sealing surface to the second sealing surface or vice versa. The sealing surfaces may be used for both gripping and applying power. The first jaw and the second jaw may each include a single sealing surface. The first jaw, the second jaw, or both may include one or more sealing surfaces or even a plurality of sealing surfaces. For example, the first jaw may include a single sealing surface and the second jaw may include two sealing surfaces. The first sealing surface and the second seal surface (e.g., sealing surfaces) may include one or more knife channels, one or more stops, or both. The first sealing surface, first jaw, second sealing surface, second jaw, or a combination thereof may include one or more knife channels. Preferably a knife channel extends through the first sealing surface and the second sealing surface so that a knife can pass through between the closed jaws.

The knife channel may function to allow a knife to extend between the jaws, when the jaws are closed. The knife channel may function to allow a knife to cut tissue or an anatomical feature of interest that is gripped between the jaws. The knife channel may extend substantially a length of the first jaw, the second jaw, or both (e.g., 90 percent or more of the length). The knife channel may extend less than a length of the first jaw, the second jaw, or both. For example, one or more stops may prevent the jaws from completely closing and the knife channel may not extend through the portion where a gap is located between the first jaw and the second jaw. The knife channels may be substantially straight (e.g., extend substantially along a longitudinal axis or parallel to a longitudinal axis of the jaws. The knife channel may have a curve. The knife channel may be located in a distal portion of the first jaw, the second jaw, or both. The knife channel may be located along about 75 percent of a length or less, about 50 of a length or less, about 40 percent of a length or less, or about 30 percent of a length or less of a first jaw, a second jaw, or both. The knife channel may be sufficiently long so that the knife can cut tissue or an anatomical feature located between or gripped between the jaws. All or a portion of the knife channel may be located between two or more stops. The stops may create a sufficient gap so that the knife may pass between the first jaw and the second jaw without inhibiting movement of the knife there between.

The one or more stops may function to create a gap between the first jaw and the second jaw. The one or more stops may function to create a gap between two conductive elements of an electrosurgical device. The one or more stops may extend between a first jaw and a second jaw. The one or more stops may function to prevent shorting between two conductive surfaces (e.g., a part of a first jaw and a part of a second jaw). The one or more stops may be located on the first jaw, the second jaw, or both. A first jaw may include some stops; a second jaw may include some stops; and both jaws may include some stops. For example, only the first jaw may include stops or only the second jaw may include stops. In another example, both the first jaw and the second jaw may include stops.

One or both of the jaws may have a plurality of stops that are fabricated from a non-conductive material. One stop, or one set of stops may be located at or near a proximal end of the jaw (e.g., proximal stops or first stops). A second stop, or set of stops, may be located further distal on the jaw than the one stops (e.g., intermediate stops or second stops). The second stop or set of stops may be shorter than the first stop or set of stops. A third stop or set of stops (e.g., distal stops or third stops) may be located further distal than the second stops and the first stops. The third set of stops may be shorter than the second set of stops. The three stops, or three sets of stops, may be configured, in height and space between stops, so that a top surface of the stops lie on a straight line. For example, when a jaw contacts a top of the stops the jaw may extend in a straight line and be in contact with each of the three stops or three sets of stops. When three or more stops or sets of stops are present (e.g., first, second, and third) a top (e.g., a portion that contacts an opposing jaw) of all of the stops may be linearly located so that an opposing jaw may contact a top of the three stops or set of three stops simultaneously without having to bend or deflect. All three stops, or set of stops, may be on the same jaw. Some of the stops, or set of stops, may be on the first jaw and the remaining stop or stops may be on the second jaw.

At least one first stop may be located on a first sealing surface and at least one second stop on the second sealing surface. There may be exactly one stop on the first surface and one stop on the second stop. The single stops may be aligned so that the stops contact each other when the jaws are moved to the second (or closed) position. An example of a leverage instrument that may be used with the stops taught herein may be found in U.S. Patent Application No. 2017/0281263, the teachings of which are expressly incorporated by reference herein for all purposes. The single first stop and single second stop may have substantially the same height (e.g., +5 percent or less). The first stop may be taller than the second stop.

The stops may be mis-aligned so that they do not contact each other when the first and second jaw are in the second position. The first stop may be configured to contact the second sealing surface and the second stop configured to contact the first sealing surface then the first jaw and the second jaw are in the second position. The first and second stop may have the same height. The first stop may be taller, (e.g. having a greater height, or having its top surface a greater distance from the surface to which the stop is affixed) than the second stop. The first stop may be configured to be proximal to the second stop when the first jaw and the second jaw are in the second position. The first stop may be configured to be distal to the second stop when the first jaw and the second jaw are in the second position.

There may be a plurality of stops on the first jaw member and at least one stop on the second jaw member. The stops may all have the same height. Some or each of the stops may have a height different than some or all of the other stops. For example, the distal tops may be shorter than both the proximate stops and the intermediate stops. At least one of the first stops may be configured to align with at least one of the second stops so as to contact each other when the jaws are in the second position. For example, a distal stop on a first jaw will contact a distal stop on a second jaw when the jaws close. All of the first stops may be configured to align with a stop on the second jaw. All of the stops on the second jaw may be configured to align with a stop on the first jaw. The stops may not be the same size or shape (e.g., each stop may have a different size, a different shape, or both). A single stop on one of the jaws may be configured to make contact with more than one stop on the other jaw. For example, an intermediate stop on a first jaw may contact with a distal stop and an intermediate stop on a second jaw.

At least one stop on the first jaw may be configured to align with at least one stop on the second jaw (e.g., a first stop, second stop, or third stop on the first jaw may align with a first stop, second stop, or third stop respectively on a second jaw). At least one stop on the first jaw may be configured to be misaligned with all stops on the second jaw. At least one of the stops on the first jaw may be configured to contact at least one stop on the second jaw. At least one stop on the first jaw is configured to contact the second sealing surface when the jaws are in the second position. The second jaw may have at least one stop that is configured to misalign with all of the stop on the first jaw so that when the first jaw and the second jaw are in the second position at least one stop on the first jaw is configured to contact at least one of the stops on the second jaw, at least one stop on the first jaw is configured to contact the second sealing surface and at least one stop on the second jaw is configured to contact the first sealing surface. Each of the plurality of stops on the first jaw member may be configured to contact the second sealing surface and all of the at least one stops on the second jaw member may be configured to contact the first sealing surface when first jaw and second jaw are the second position (e.g., closed position or clamped position). Each of the plurality of stops on the first jaw member or on the first surface, and the at least one stop on the second jaw member may have the same height (e.g., may extend a distance above a surface that the stop is in contact with). Some or all of the plurality of stops on the first jaw member and the at least one stop on the second member may have a height that is different from some or all of the remaining stops. Variants in stop positioning, alignment, height, or a combination thereof may allow for numerous options for tailoring the size and shape of the gap between the first sealing surface and the second sealing surface when the jaws are in the second position to customize the desired tissue processing capabilities of the device.

The device may comprise a first jaw with a plurality of stops and a second jaw. The plurality of stops may comprise a first stop or a plurality of first stops and a second stop or a plurality of second stops. The first stop or the plurality of first stops may have a greater height than the second stop or any or all of the plurality of second stops. The first stop or plurality of first stops may be positioned proximally to the second stop or plurality of second stops. The first stop or plurality of first stops may be positioned distally to the second stop or plurality of second stops. The distal stops may be higher than the proximal stops so that a gap at the distal end region is larger that the gap at the proximal end region. The second jaw may not have any stops. The second jaw may have at least one stop. One, some, all, or none of the at least one stop on the second jaw may be configured to contact one or more of the stops on the first jaw.

The device may comprise a first jaw with a plurality of stops and a second jaw. The plurality of stops may comprise a first stop or a plurality of first stops, a second stop or plurality of second stops, and a third stop or a set of third stops. The first stop or plurality of first stops may be located at a first position on the jaw (e.g., in a distal region of one or more of the jaws). The third stop or plurality of third stops may be located proximal of the first stops (e.g., in a proximal region of the one or more of the jaws). The second stop or plurality of second stops may be located between the first stops and the third stops (e.g., located distal to the third stop and proximal to the first stop). The first stop and the third stop may have a different height. The second stop may have a height between the heights of the one or more first stops and the one or more third stops. The first stops (e.g., distal stops) may be taller than the third stops (e.g. proximal stops). Alternately the first stops (e.g., distal stops) may be shorter than the third (e.g. proximal stops). The heights and the location of the stops may be configured so that the tops of the first stops, second stops, and third stops fall on a straight line. There may be additional stops, or sets of stops. For example, there may be a fourth stop, or set of fourth stops, positioned between the first stops and third stops, and configured to have a height between the heights of the first stops and the third stops.

The stops may be comprised of or include an incompressible material. Some or all of the stops may be comprised of or include a compressible material. Some or all of the stops may include both an incompressible material and a compressible material. For example, during a gripping of tissue or an anatomical feature between the first jaw and the second jaw the compressible material may elastically deform so that other stops may be moved into contact with the tissue or anatomical feature and the incompressible material may prevent the jaws from being closed beyond a predetermined distance. The jaws may elastically deform so that all of the stops are moved into contact with another stop, an opposing jaw, a sealing surface, or a combination thereof. Some or all of the plurality of stops on the first jaw member and the at least one stop on the second member may have a compressibility that is different from some or all of the compressibility of the stops. Compressibility may be a function of the compliance and size of the stops. For example, a stop with a larger height may have a compressibility that is greater than a stop with a lower height. The stops may be made of a non-conductive material, an insulative material, or both. The stop members may be affixed/attached to the jaw member(s) by stamping, thermal spraying, over molding, an adhesive, heat steaking, ultrasonic welding, friction welding, or a combination thereof. The stop members may project from the inner-facing surface of at least one of the jaw members or each of the jaw members. The stop members may be made from or include an insulative material such as parylene, nylon and/or ceramic. The stop members may be made of or include silica, or alumina, titania, syndiotactic polystryrenes such as QUESTRA® manufactured by DOW Chemical, Syndiotactic-polystyrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamideimide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate. The stop members may have good toughness, abrasion resistance, thermal insulation, biocompatibility, or a combination thereof. The one or more stops may form a knife channel that a knife extends through, a gap between the first jaw and the second jaw, or both.

The gap may function to prevent a first jaw and a second jaw from contacting each other, create a dielectric space between the first jaw and second jaw, prevent shorting of the first jaw and the second jaw, or a combination thereof. The gap may be a distance from a first sealing surface to a second sealing surface. The gap may be a distance from an internal surface of a first jaw to an internal surface of a second jaw. The gap may create a space so that tissue or a feature of interest that may be captured between the first jaw and the second jaw is not damaged when the tissue or the feature of interest is gripped between the jaws. The gap may be sufficiently large so that the first jaw and second jaw are not shorted when the first jaw and the second jaw are closed and tissue or a feature of interest is not located between the first jaw and the second jaw. The gap may vary linearly. The gap may vary non-linearly. The jaws may be flexible and the gap may vary based upon a height of the stops when the jaws are in the second position or the closed position. The gap may have two parallel sides or boundaries (e.g., the jaws or sealing surfaces). The gap may have sides that converge as the sides extend distally. The gap may have sides that diverge as the sides extend distally. The gap may have sides that converge as the sides extends proximally. The gap may have sides the diverge as the sides extend proximally. An intermediate region may be a thickest portion of a gap. The intermediate region may be a thinnest portion of a gap. The intermediate region may have a height that is between the distal end region and the proximal end region. The gap may be a distance between the first jaw and the second jaw of about 0.025 mm or more, about 0.05 mm or more, about 0.075 mm or more, or about 0.1 mm or more. The gap may be a distance between the first jaw and the second jaw of about 3 mm or less, about 2 mm or less, about 1 mm or less, about 0.5 mm or less, or about 0.2 mm or less (e.g., about as recited for height or cross-sectional length (e.g., diameter) may be ±0.05 mm or less or preferably about ±0.03). The gap may vary based upon location. For example, a gap in the distal end region may be about 0.08 mm and in the proximal end region may be about 0.13 mm and about 0.1 mm in the intermediate region. The gap may be determined by a height of one stop. For example, if a gap is about 0.2 mm then the stop has a height of about 0.2 mm. The gap may be determined by two opposing stops contacting each other. For example, if the gap is about 0.1 mm then each of two stops have a height of about 0.05 mm. The height of the opposing stops may be evenly distributed. The height of the opposing stops may be unevenly distributed. One stop may be about 50 percent or more, about 60 percent or more, about 70 percent or more, about 80 percent or more, or about 95 percent or less of a height of the gap. Opposing stops may be made of a same material. Opposing stops may be made of different materials or a portion of one stop may be made of a different material than an opposing stop. When more than one stop is present all of the stops may be located on one jaw. Some of the stops may be located on the first jaw and some of the stops may be located on the second jaw. Then a plurality of stops are located on opposing jaws at least one set of stops may be aligned. Stops may only be aligned in the distal end region, the intermediate region, or the proximal region. Some or all of the stops may be aligned in the distal end region, the intermediate region, the proximal region, or a combination thereof. When stops are located on the first jaw and the second jaw some or all of the stops may be aligned so that when the jaws are closed the stops contact each other. Preferably, some of the stops may be aligned or opposing and some of the stops may be free of an opposing stop. All of the stops may be staggered from one another. The stop may be staggered laterally (e.g., from side to side), longitudinally (e.g., from distal to proximal), or both. The stops may be symmetrically located on the jaws. The stops may be asymmetrically located on the jaws. The stops may be located in straight lines. The stops may be located in patterns. The stops may be randomly located on the jaws. The stops when opposed may only be partially opposed. For example, half of one stop may contact half of an opposing stop. One stop may contact at least a portion of two opposing stops. The stops may be all the same size and shape. The stops may be of different sizes, different shapes, or both. The stops may have a cross-sectional shape that is circular, oblong, triangular, oval, diamond, square, pentagonal, octagonal, a heptagon, heptagon, or a combination thereof. A cross-sectional shape of the stops may be free of points or flat wall. The stops may have a planar top surface (e.g., the top of the stops may be flat). The stops may be free of a planar top. The stops may have a point. The stops may have a diamond point (e.g., 4 walls that converge at a point), a triangular point (e.g., two walls that converge at a point, a cone point (e.g., a circular wall that narrows in diameter to a point), a spherical top, or a combination thereof. The gap may vary along a length of the jaws. The gap may be smallest at a proximal end region (e.g., a location proximate to a third stop or proximal stop) and largest at a distal end region (e.g., a location proximate to a first stop or distal stop). Preferably, the gap may be smallest at a distal end region and largest at a proximal end region. The gap at the distal end region may be about. 01 mm or more, about 0.02 mm or more, about 0.03 mm or more, about 0.05 mm or more, about. 07 mm or more, or about 0.08 mm or more. The gap at the distal end region may be about 1 mm or less, about 0.5 mm or less, about 0.3 mm or less, about 0.2 mm or less, or about 0.1 mm or less (e.g., about as recited for height or cross-sectional length (e.g., diameter) may be +0.05 mm or less or preferably about +0.03).

The gap in an intermediate region (e.g., a region between the proximal end and the distal end, proximate to an intermediate stop or second stop, or both) may be the same as a distal end region, a proximal end region, or both. The gap in an intermediate region may have a largest height when compared to the distal end region and the proximal end region. The gap in the intermediate region may have smallest height when compared to the distal end region and the proximal end region. Preferably, the gap in the intermediate region may be between the height of the distal end region and the proximal end region. For example, the gap in the distal end region may be larger than both the intermediate region and the gap in the proximal end region and the intermediate region may be larger than the proximal end region. For example, gap in the proximal end region may be larger than both the intermediate region and the gap in the distal end region and the intermediate region may be larger than the distal end region. The gap in the intermediate region may be about 0.01 mm or more, about 0.03 mm or more, about 0.05 mm or more, about 0.075 mm or more, about 0.1 mm or more, or about 0.13 mm or more. The gap in the intermediate region may be about 5 mm or less, about 3 mm or less, about 1 mm or less, about 0.5 mm or less, about 0.05 mm or less, or about. 005 mm or less. The gap in the intermediate region may be controlled in dependently of the gap in the proximal end region and the distal end region.

The gap in the proximal end region (e.g., a region closest to the joint between the jaws or proximate to the third stop or proximal stop) may be a largest gap when compared to the gaps in the intermediate region, the distal region, or both. The gap in the proximal end region may prevent tissue from being pinched, damaged, or both. The gap in the proximal end region may assist in creating an even pressure across the tissue located between the first jaw and the second jaw. The gap in the proximal end region may be the same as the gaps in the intermediate region and the distal end region. The gap in the proximal end region may be the smallest when compared to the gaps in the distal end region and the intermediate region. The gap in the proximal end region may be the largest when compared to the gaps in the intermediate region and the distal end region. The gap in the proximal region may be about 0.01 mm or more, about 0.03 mm or more, about 0.05 mm or more, about 0.075 mm or more, about 0.1 mm or more, or about 0.13 mm or more. The gap in the proximal region may be about 5 mm or less, about 3 mm or less, about 1 mm or less, about 0.5 mm or less, about 0.3 mm or less, or about 0.2 mm or less. The gap may form a portion of the knife channel.

One or more knives may extend through the knife channel, between the stops, or both. The one or more knives may be made of metal, a conductive material, or both. The one or more knives may mechanically cut tissue, an anatomical feature of interest, a feature of interest, a vein, an artery, or a combination thereof. The one or more knives may include a sharpened edge that may be used for cutting. The one or more knives may electrically cut, cauterize, or both tissue, an anatomical feature of interest, a feature of interest, a vein, an artery, or a combination thereof. The one or more knives may extend to a location between the jaws (e.g., proximal of a distal end of the jaws). The one or more knives may extend to a location distal of an end of the jaws. The one or more knives may have a blade that has a height that extends normal to a surface, a gripping surface, a sealing surface, or a combination thereof of the jaws. The knife may extend along a center of the jaws. The knife may extend through a combination of a knife channel and stops.

The device taught herein may include one or more of the features taught herein: wherein the at least one first stop members protrudes a first distance from the first seal surface and the at least one second stop member protrudes a second distance from the second seal surface, the first distance being greater than the second distance; wherein the at least one first stop members protrudes a first distance from the first seal surface and the at least one second stop member protrudes a second distance from the second seal surface, the first distance is the same as the second distance; wherein at least one of the first or second jaw members is movable relative to the other jaw member from a first position wherein the first and second jaw members are disposed in spaced relation relative to one another to a second position wherein the first and second jaw members are closer to one another; wherein the at least one first stop member is proximal to the at least one second stop member when the first jaw member and the second jaw member are in the second position; wherein at least one of the first stop members, at least one of the second stop members, or both, are made from a non-conductive material; wherein the at least one first stop members is made from a first material and the at least one second stop members is made from a second material that is different from the first material; wherein the at least one first stop members is made from a first material and the at least one second stop members is made from a second material, the first material is the same as the second material; wherein at least one of the first stop members, at least one of the second stop members, or both, are configured to enhance manipulation or gripping of tissue held between the first and second seal surfaces; wherein at least one of first stop members, at least one of the second stop members, or both, is configured to prevent short circuiting of the first and second seal surfaces; wherein at least one of first stop members, at least one of the second stop members, or both, is configured to maintain space between the first and second seal surfaces in the second position of the first and second jaw members; wherein the first stop members define a first diameter and wherein the second stop member defines a second diameter, the first diameter is different from the second diameter; wherein the second stop members are configured to contact the first seal surface without the plurality of first stop members contacting the second sealing surface; wherein at least one second stop members are positioned opposing the first stop members to combine creating opposing stop members of generally a greater combined protrusion than those placed upon the first or second seal surface; wherein the second stop members are made from a conductive material; wherein the first stop members, the second stop members, or both, are configured to enhance manipulation and gripping of tissue held between the first and second seal surfaces; wherein at least the second stop member is configured to prevent short circuiting of the first and second seal surfaces; wherein the plurality of first stop members are configured to maintain space between the first and second seal surfaces in the second position of the first and second jaw members; wherein the second stop members are configured to contact the first stop members without the plurality of first stop members contacting the second sealing surface; wherein the first stop members provide a first compressibility from the first seal surface and the second stop members provide a second compressibility from the second seal surface; wherein the first stop members, the second stop members, or both are made from a non-conductive material; wherein the first stop members are made from a first material and the second stop members are made from a second material that is different from the first material; wherein the first stop members are made from a first material and the second stop members are made from the same material as the first stop members; wherein the first stop members, the second stop members, or both, are configured to enhance manipulation and gripping of tissue held between the first and second seal surfaces; wherein at least the second stop member is configured to prevent short circuiting of the first and second seal surfaces; wherein the first stop members, the second stop member, or both, are configured to maintain space between the first and second seal surfaces in the second position of the first and second jaw members; wherein the first stop members define a first diameter and wherein the second stop member defines a second diameter different from the first; wherein the second stop members are configured to contact the first seal surface without the plurality of first stop members contacting the second sealing surface; wherein the second stop members generally have the same compression as the first stop members; wherein the first stop members are made from a first material and the second stop members are made from the same material as the first stop members; and wherein the first stop members define a first diameter and wherein the second stop member defines a second diameter and the first diameter is different than the second diameter.

FIG. 1 illustrates an electrosurgical device 2 that as shown is as electrosurgical forceps 4. The electrosurgical forceps 4 include a housing 10 that an elongated shaft 12 extends from. Forceps 20 are located at an end of the elongated shaft 12 and as shown the forceps 20 are closed.

Figure 2:
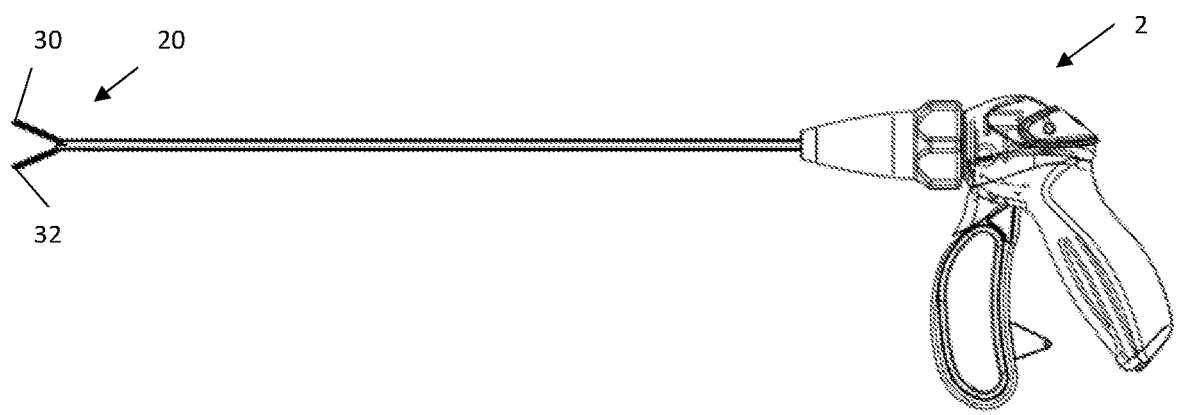
FIG. 2 is a side view of the device with the jaws in the open position.

FIG. 2 illustrates the electrosurgical device 2 with the forceps 20 in an open position. The first jaw 30 and the second jaw 32 of the forceps 20 are open so that a feature of interest (not shown) can be gripped therebetween.

Figure 3:
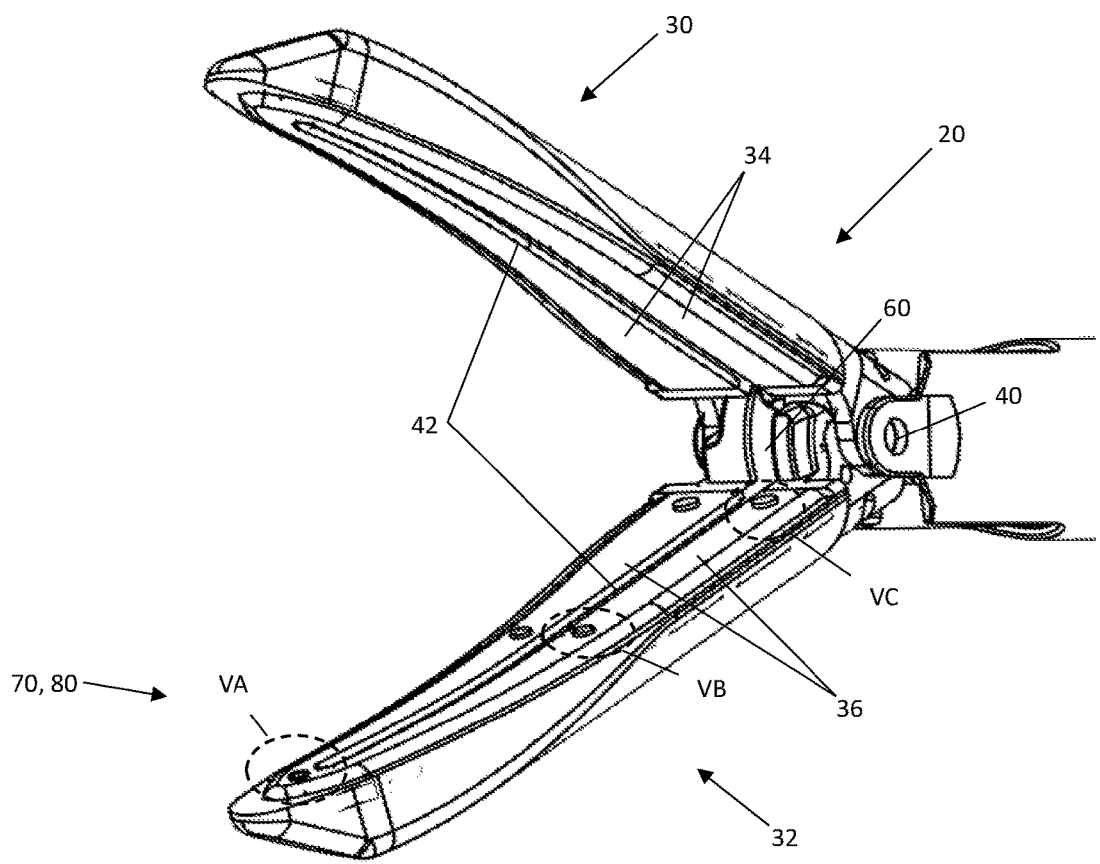
FIG. 3 is a distal perspective view of the inside of the jaws and sealer divider.

FIG. 3 is a close-up view of the forceps 20 with the first jaw 30 and the second jaw 32 spaced apart. The first jaw 30 includes a first sealing surface 34 and the second jaw 32 includes a second sealing surface 36 with a knife channel 42 extending therein so that a knife 60 can extend between the first jaw 30 and the second jaw 32 when the jaws are closed. The first jaw 30 and the second jaw 32 move about a pivot member 40. The second jaw 32 includes a sealer divider 70, which as shown are a plurality of stops 80 on the second sealing surface 36.

Figure 4:
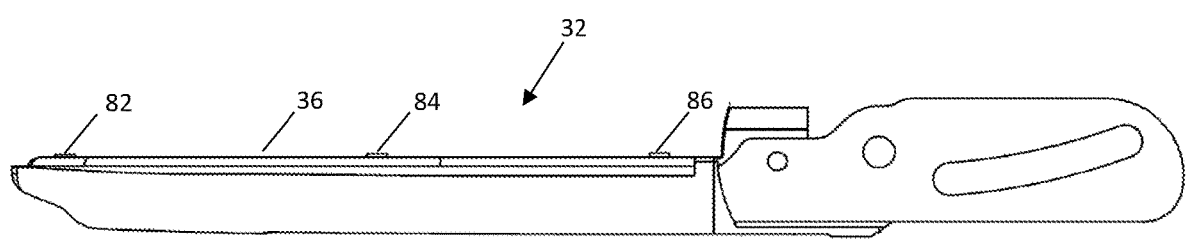
FIG. 4 is a side view of a first jaw shown in FIG. 3.

FIG. 4 is a side view of the second jaw 36. The second jaw 36 has a second sealing surface 36 with a first stop (distal stop) 82, a second stop (intermediate stop) 84, and a third stop (proximal stop) 86.

Figure 5A:
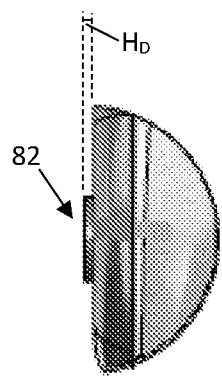
FIG. 5a is detailed views of a segment shown in FIG. 4 at location VA.

FIG. 5a is a cut out view of the first stop 82 of FIG. 3 depicting that the first stop 82 has a height HD.

Figure 5B:
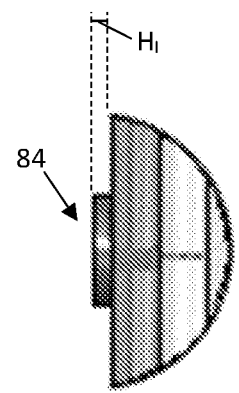
FIG. 5b is detailed views of a segment shown in FIG. 4 at location VB.

FIG. 5b is a cut out view of the second stop 84 of FIG. 3 depicting that the second stop 84 has a height HI.

Figure 5C:
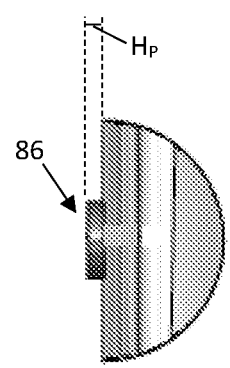
FIG. 5c is detailed views of a segment shown in FIG. 4 at location VC.

FIG. 5c is a cut out view of the third stop 86 of FIG. 3 depicting that the third stop 86 has a height Hp.

Figure 6:
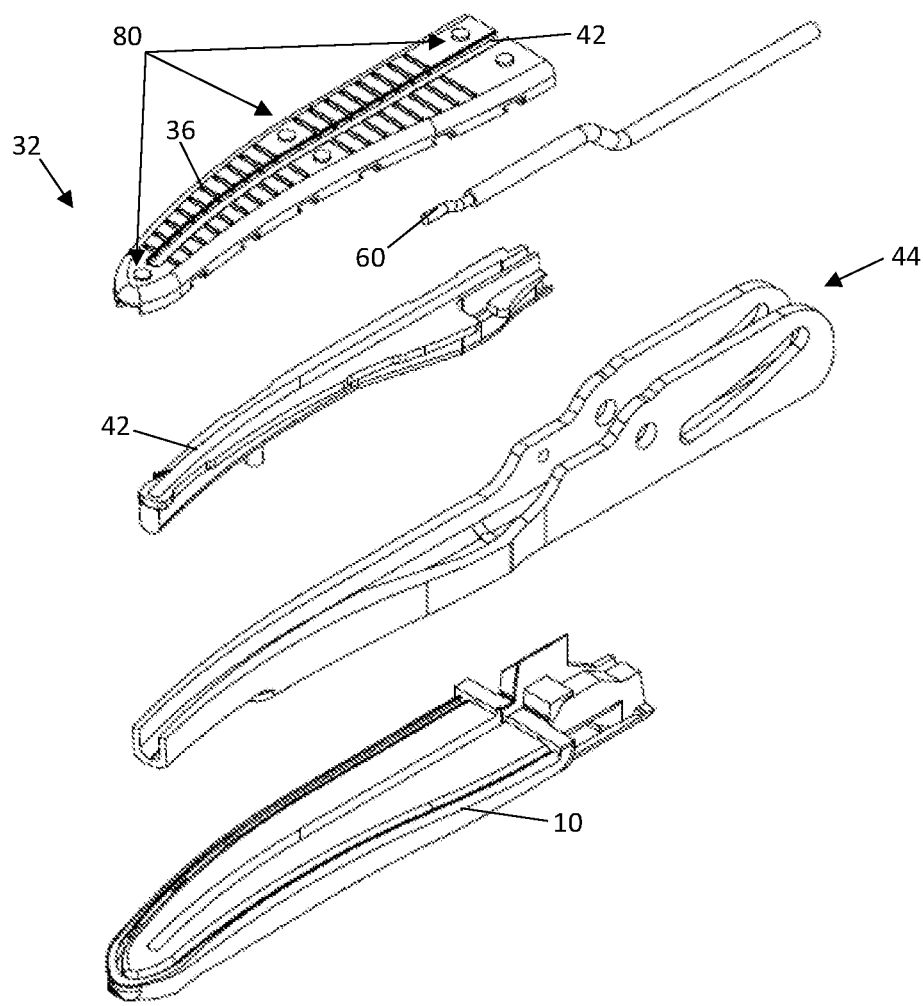
FIG. 6 is an exploded view of a jaw.

FIG. 6 is an exploded view of a second jaw 32. The second jaw 32 is a housing 10 that forms a bottom of the second jaw 32. A jaw arm 44 is located above the housing 10 and below a knife channel 42 and second sealing surface 36. The second sealing surface also includes a knife channel 42 that the knife 60 extends through. The sealing surface 36 includes the stops 80.

Figure 7:
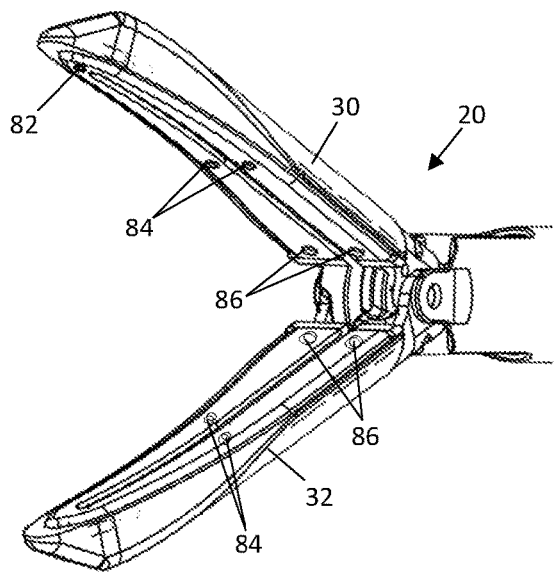
FIG. 7 is a distal perspective view of the jaws and a sealer divider.

FIG. 7 illustrates the forceps 20 in an open position where the first jaw 30 and the second jaw 32 are spaced apart. The first jaw 30 includes a first stop 82, second stops 84, and third stops 86. The second jaw 32 only includes second stops 84 and third stops 86.

Figure 8:
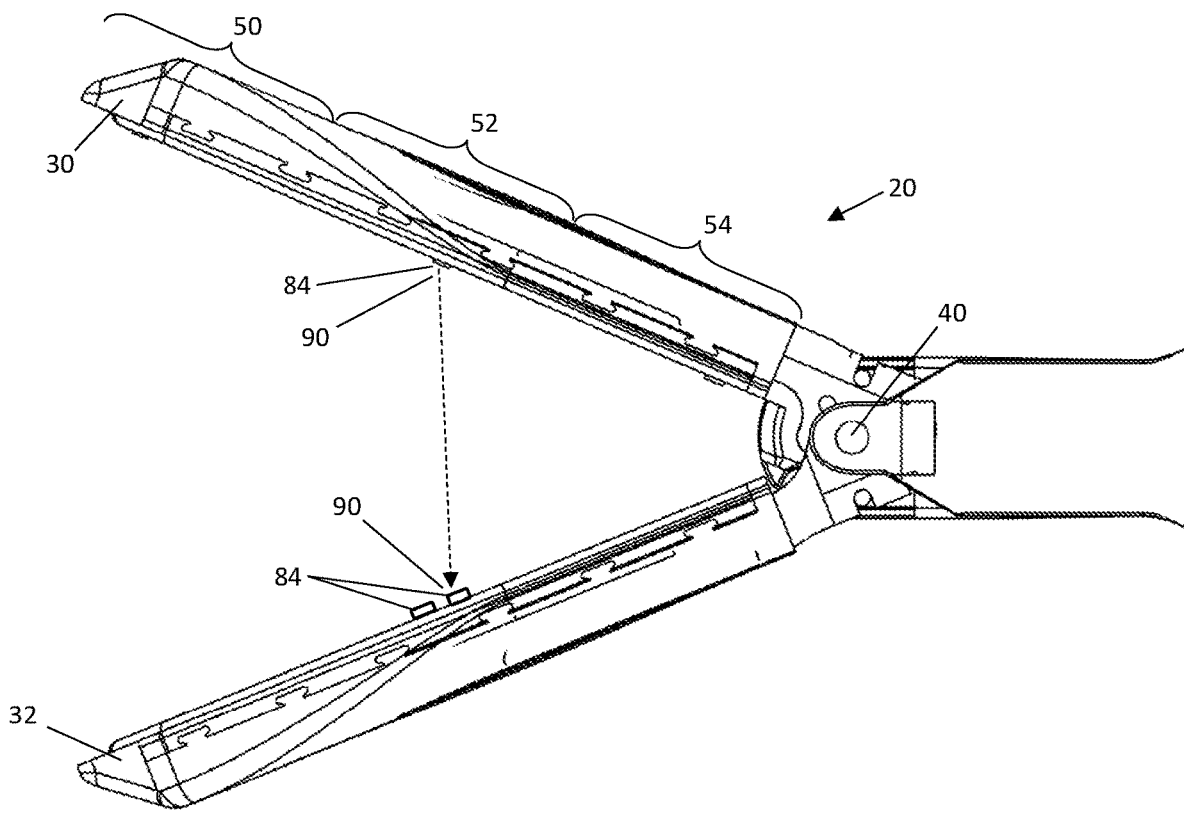
FIG. 8 is a side view of jaws and a sealer divider.

FIG. 8 illustrates the forceps 20 with the first jaw 30 and the second jaw 32 pivoted about a pivot member 40 to an open position. The first jaw 30 and the second jaw 32 each have a distal end region 50, intermediate region 52, and a proximal end region 54. The first jaw 30 includes a second stop 84 that is an opposing stop 90 to a second stop 84 on the second jaw 32, which is also an opposing stop 90. The second jaw 32 also includes a second stop 84 that is not located opposite any other stops. All of the second stops 84 are the same size and height.

Figure 9:
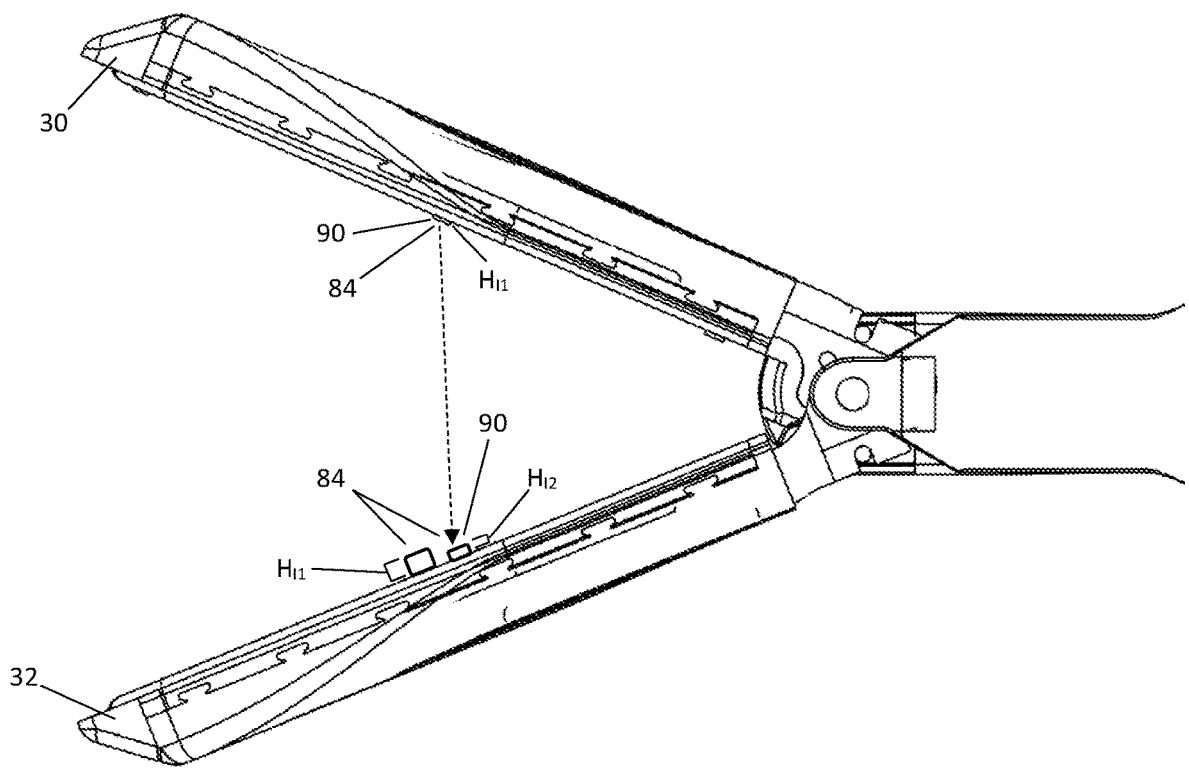
FIG. 9 is a side view of jaws and a sealer divider with different height stops.

FIG. 9 illustrates a first jaw 30 and a second jaw 32 in an open position. The first jaw includes a second stop 84 and the second jaw includes two second stops 84. The second stop 84 on the first jaw is an opposing stop 90 to one of the second stops 84 on the second jaw 32 so that the second stop 84 on the second jaw 32 is an opposing stop 90. The opposing stop 90 on the second jaw 32 has a first height ($H_{I1}$) and the second stop 84 that is not opposed has a second height ($H_{I2}$) that is equal in height to the two opposing stops 90 when the two opposing stops 90 are in contact.

Figure 10A:
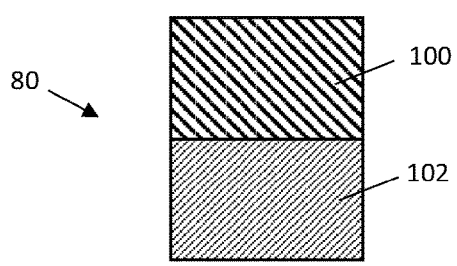
FIG. 10A illustrates a stop made of two materials.

FIG. 10A is a side view of a stop 80 made of a first material 100 and a second material 102.

Figure 10B:
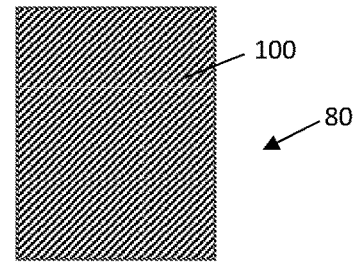
FIG. 10B illustrates a stop made of a material.

FIG. 10B is a side view of a stop 80 of a first material 100.

Figure 11A:
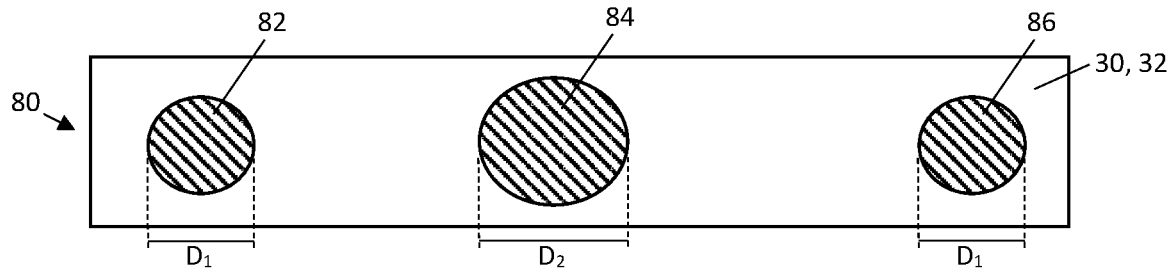
FIG. 11A illustrates a variation in sizes of the stops in each region.

FIG. 11A illustrates a configuration of the stops 80 on the first jaw 30 and/or second jaw 32. The stops 80 include a first stop 82 having a first diameter ($D_1$), a second stop 84 having a second diameter ($D_2$), and third stop 86 having a first diameter ($D_1$).

Figure 11B:
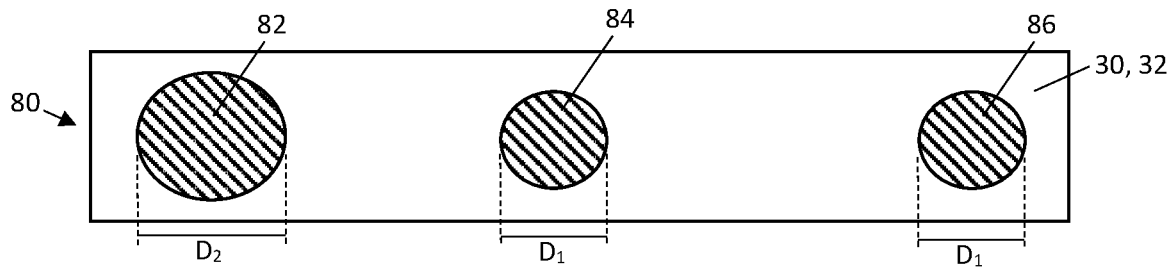
FIG. 11B illustrates a variation in sizes of the stops in each region.

FIG. 11B illustrates a configuration of the stops 80 on the first jaw 30 and/or second jaw 32. The stops 80 include a first stop 82 having a second diameter ($D_2$), a second stop 84 having a first diameter ($D_1$), and third stop 86 having a first diameter ($D_1$).

Figure 11C:
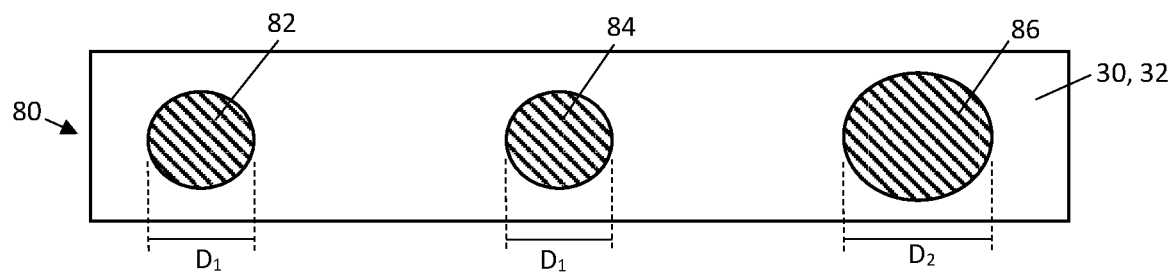
FIG. 11C illustrates a variation in sizes of the stops in each region.

FIG. 11C illustrates a configuration of the stops 80 on the first jaw 30 and/or second jaw 32. The stops 80 include a first stop 82 having a first diameter ($D_1$), a second stop 84 having a first diameter ($D_1$), and third stop 86 having a second diameter ($D_2$).

Figure 12A:
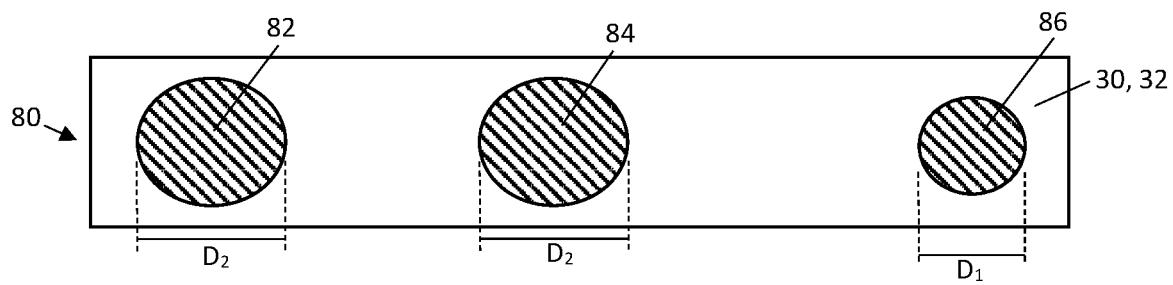
FIG. 12A illustrates a variation in sizes of the stops in each region.

FIG. 12A illustrates a configuration of the stops 80 on the first jaw 30 and/or second jaw 32. The stops 80 include a first stop 82 having a second diameter ($D_2$), a second stop 84 having a second diameter ($D_2$), and third stop 86 having a first diameter ($D_1$).

FIG. 12B illustrates a configuration of the stops 80 on the first jaw 30 and/or second jaw 32. The stops 80 include a first stop 82 having a first diameter ($D_1$), a second stop 84 having a second diameter ($D_2$), and third stop 86 having a second diameter ($D_2$).

FIG. 12C illustrates a configuration of the stops 80 on the first jaw 30 and/or second jaw 32. The stops 80 include a first stop 82 having a second diameter ($D_2$), a second stop 84 having a first diameter ($D_1$), and third stop 86 having a second diameter ($D_2$).

FIG. 13A illustrates the stops 80 within the distal end region 50, the intermediate region 52, and/or the proximal end region 54 where all of the stops are in a straight line and are a same size and shape.

FIG. 13B illustrates the stops 80 within the distal end region 50, the intermediate region 52, and/or the proximal end region 54 where one stop 80 is out of line with the other stops 80. Some of the stops 80 have a first shape 110 and some of the stops 80 have a second shape 112. As shown the first shape 110 is a circle and the second shape 112 is a diamond.

FIG. 13C illustrates the stops 80 within the distal end region 50, the intermediate region 52, and/or the proximal end region 54 where the stops 80 are in-line but some of the stops 80 have a portion that extends out of line. The stops 80 have a first shape 110 and a second shape 112 where the first shape 110 is circular and the second shape 112 is an oval.

Figure 14A:
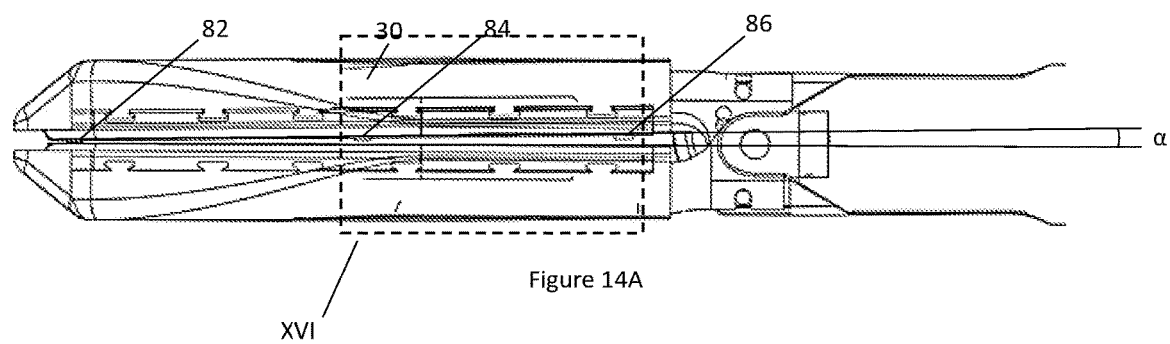
FIG. 14A illustrates one way of creating a gripping force where the distal stops are contacted first.

FIG. 14A illustrates the first jaw 30 and the second jaw 32 partially or fully closed and extend at an angle ($\alpha$) relative to each other. The first stop 82 is in contact with the second jaw 32 and a space(S) is present between the second jaw 32 and both the second stop 84 and the third stop 86.

Figure 14B:
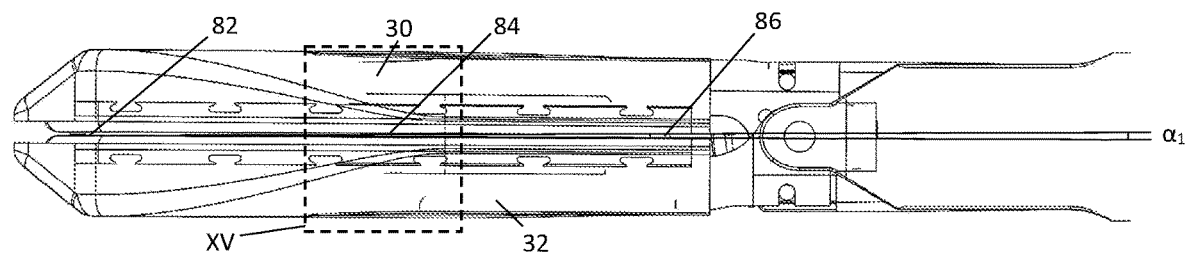
FIG. 14B illustrates where all of the stops are being contacted and a straight line is formed along a face of each of the jaws.

FIG. 14B illustrates the first jaw 30 and the second jaw 32 in a closed position where the first jaw 30 and the second jaw 32 extend at an angle ($\alpha_1$) relative to each other. The first stop 82, second stop 84, and third stop 86 are all in contact with the first jaw 30 and the second jaw 32. The first stop 82 has a height that is less than the second stop 84 and the third stop 86. The second stop 84 has a height that is less than the third stop 86. The height differences between the stops create the angle ($\alpha_1$) between the first jaw 30 and the second jaw 32, which is less than the angle ($\alpha$) of FIG. 14A.

Figure 15:
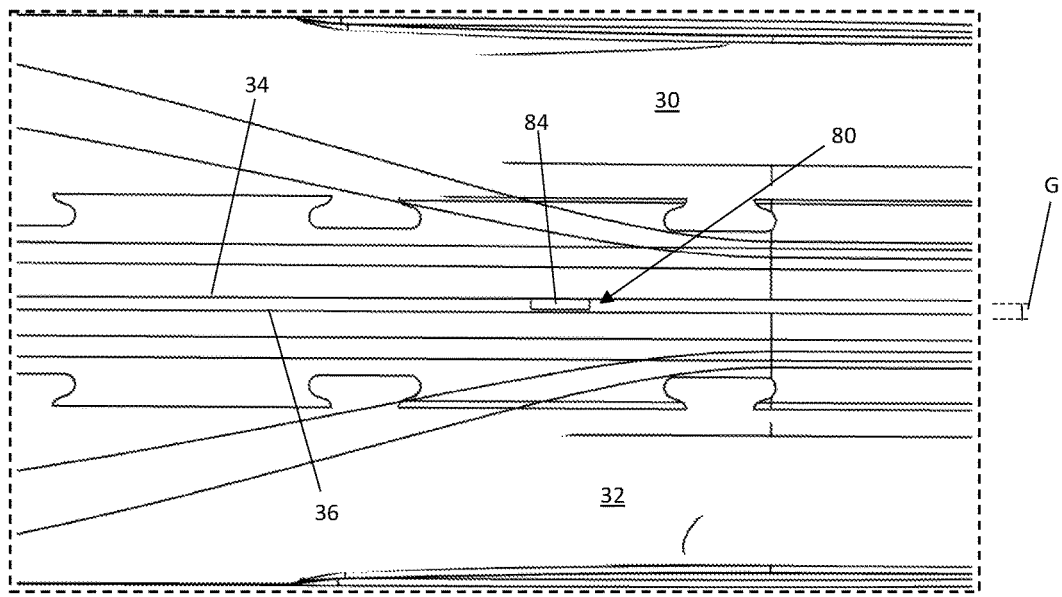
FIG. 15 is a close-up view of the gap and second stop shown in box XV of FIG. 14B.

FIG. 15 is a close-up view of a stop 80 in the box XV of FIG. 14B. The stop 80 is a second stop 84 that extends from a first jaw 30 to a second jaw 32. The first jaw 30 has a first sealing surface 34 and a second jaw 32 with a second sealing surface 36. The second stop 84 creates a gap (G) that extends from a face of the first sealing surface 34 to a face of the second sealing surface 36.

Figure 16:
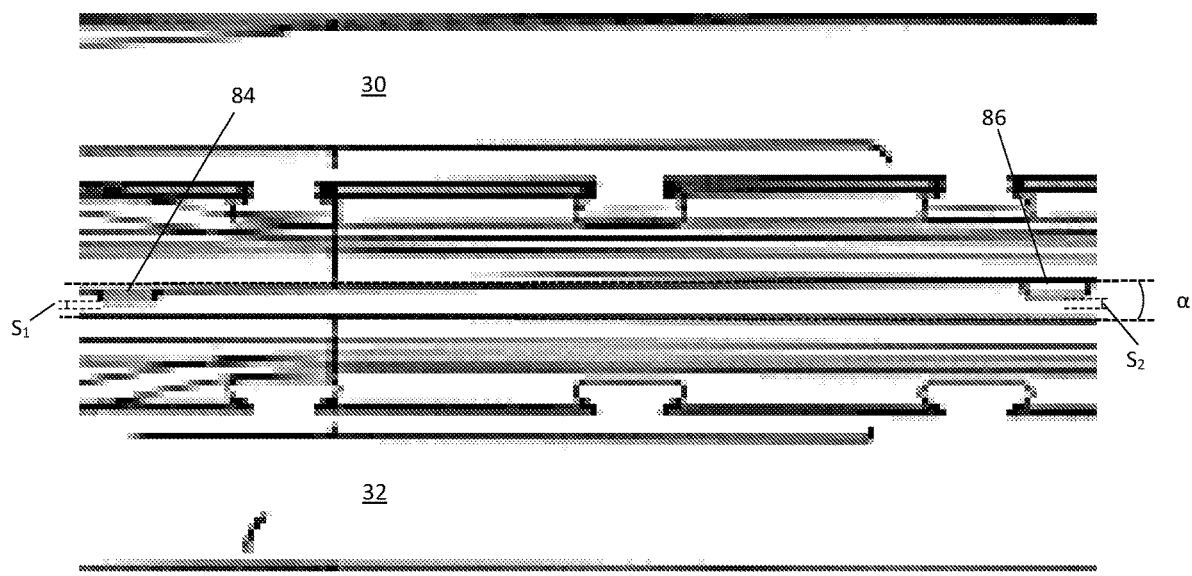
FIG. 16 is a close-up view of the spaces between the second stop and the second jaw and the third stop and the second jaw shown in box XVI of FIG. 14A.

FIG. 16 is a close-up view of the spaces between the stops on the first jaw 30 and the second jaw 32. The second stop 84 has a space (S1) from the second jaw 32 when the jaws are partially or fully closed and the third stop 86 has a space (S2). The first jaw 30 and the second jaw 32 are spaced apart by an angle ($\alpha$).

As used herein, unless otherwise stated, the teachings envision that any member of a genus (list) may be excluded from the genus; and/or any member of a Markush grouping may be excluded from the grouping.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01, or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the of a range in terms of "at least 'x' parts by weight of the resulting composition" also contemplates a teaching of ranges of same recited amount of "x" in percent by weight of the resulting composition."

The components express their composition in a percent by weight. Even through the compositions do not express a relative ratio between components such ratios are within the scope of the teachings. By way of example, if element A is in an amount of about 10 percent by weight and element B is in an amount of about 2 percent by weight of the total composition the teachings herein contemplate a ratio of about 4:1 for A to B. Unless otherwise stated, all ranges include both endpoints and all numbers between the endpoints. Unless otherwise stated, a teaching with the term "about" or "approximately" in combination with a numerical amount encompasses a teaching of the recited amount, as well as approximations of that recited amount. By way of example, a teaching of "about 100" encompasses a teaching of within a range of 100+/−15.

The disclosures of all articles and references, including patent applications and publications, are incorporated by reference for all purposes. The term "consisting essentially of to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist of, or consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Electrosurgical device
4 Electrosurgical forceps
10 Housing
12 Elongated shaft
20 Forceps 30 First Jaw
32 Second jaw
34 First sealing surface
36 Second sealing surface
40 Pivot member
42 Knife channel
44 Jaw arm
50 Distal end region
52 Intermediate end region
54 Proximal end region
60 Knife
70 Sealer Divider
80 Stops
82 First stop (e.g., distal stops)
84 Second stop (e.g., intermediate stops)
86 Third stop (e.g., proximal stops)
H Height of stops
90 Opposing stops
100 First material
102 Second material
110 First shape
112 Second shape
G Gap

We claim:

1. A device comprising:
   a first jaw having a gripping surface;
   a second jaw having a gripping surface, the second jaw being spaced apart from the first jaw and being configured to move between an open position and a closed position; and
   a sealer divider having a plurality of stops extending beyond the gripping surface of the first jaw or the gripping surface of the second jaw, the plurality of stops including at least:
      one or more distal stops having a height;
      one or more proximal stops having a height; and
      a plurality of intermediate stops including at least a first intermediate stop located on the first jaw and a second intermediate stop located on the second jaw in an opposed position so that when the first jaw and the second jaw are closed, the first intermediate stop contacts the second intermediate stop to have a combined height that is greater than the height of the one or more distal stops and the height of the one or more proximal stops;
   wherein the first and second jaws are flexible and configured to elastically deform during a gripping of tissue or an anatomical feature therebetween;
   wherein the plurality of stops are non-conductive;
   wherein the first jaw and the second jaw have a proximal end and a distal end; and
   wherein contact between the first intermediate stop and the second intermediate stop produces a gap that is widest at the proximal end and narrowest at the distal end.

2. The device of claim 1, wherein the one or more distal stops are made from a first material and the one or more proximal stops, the plurality of intermediate stops, or both are made from a second material that is different from the first material.

3. The device of claim 1, wherein the one or more distal stops are made from a first material and the one or more proximal stops, the plurality of intermediate stops, or both are made from a second material that is a same material as the first material.

4. The device of claim 1, wherein at least one of the one or more distal stops, the one or more proximal stops, the plurality of intermediate stops, or a combination thereof are configured to prevent short circuiting of the first jaw and the second jaw.

5. The device of claim 1, wherein a height of the plurality of intermediate stops is greater than the height of the one or more distal stops.

6. The device of claim 5, wherein the first jaw includes one distal stop, two proximal stops, and two intermediate stops.

7. The device of claim 1, wherein all of the one or more distal stops and all of the one or more proximal stops have a same height.

8. The device of claim 1, wherein the plurality of intermediate stops are located substantially equidistant between the one or more distal stops and the one or more proximal stops.

9. The device of claim 1, wherein the one or more distal stops have a first diameter and the plurality of intermediate stops have a second diameter, with the first diameter being different from the second diameter.

10. The device of claim 1, wherein the one or more distal stops, the plurality of intermediate stops, or both, are configured to enhance manipulation and gripping of tissue held between the first and second gripping surfaces.

11. The device of claim 1, wherein at least the plurality of intermediate stops are configured to prevent short circuiting of the first gripping surface and the second gripping surface.

12. The device of claim 1, wherein the one or more distal stops provide a first compressibility and the plurality of intermediate stops, the one or more proximal stops, or both provide a second compressibility that is different from the first compressibility.

13. The device of claim 12, wherein the first compressibility is less than the second compressibility so that if the second compressibility is overcome the first compressibility prevents contact between the first jaw and the second jaw.

14. The device of claim 1, wherein the one or more distal stops and the plurality of intermediate stops generally have a same compression.

15. The device of claim 1, wherein the one or more distal stops and the one or more proximal stops are located on the first jaw.

16. The device of claim 1, wherein the one or more distal stops are located only on the first jaw and the one or more proximal stops are located only on the second jaw.

17. A device comprising:
    a first jaw having a gripping surface, a proximal end, and a distal end;
    a second jaw having a gripping surface, a proximal end, and a distal end, the second jaw being spaced apart from the first jaw and being configured to move between an open position and a closed position; and
    a sealer divider having a plurality of stops that protrude beyond the gripping surface of the first jaw or the gripping surface of the second jaw, the plurality of stops including at least:
       one or more distal stops having a height;
       one or more proximal stops having a height; and
       one or more intermediate stops located on the first jaw and the second jaw with some of the one or more intermediate stops being located in an opposed position so that when the first jaw and the second jaw are closed the some of the one or more intermediate stops on the first jaw contact the some of the one or more intermediate stops on the second jaw to have a combined height that is greater than the height of the one or more distal stops and the height of the one or more proximal stops, and to produce a gap that is widest at the proximal end of the first and second jaws and narrowest at the distal end of the first and second jaws;

wherein the plurality of stops are non-conductive and the one or more distal stops, the one or more proximal stops, or both are distributed on the gripping surface of the first jaw, the gripping surface of the second jaw, or both.

18. The device of claim 17, wherein some of the one or more intermediate stops are free of contact with another of the one or more intermediate stops.

19. The device of claim 18, wherein the some of the one or more intermediate stops that are free of contact have a height equal to the combined height of the one or more intermediate stops that are opposed.

20. The device of claim 18, wherein the some of the one or more intermediate stops that are free of contact have a height less than the combined height of the one or more intermediate stops that are opposed.

21. The device of claim 17, wherein the one or more distal stops are made from a first material and the one or more proximal stops, the one or more intermediate stops, or both are made from a second material that is different from the first material.

\* \* \* \* \*